(12) United States Patent
Nevyas

(10) Patent No.: US 6,217,570 B1
(45) Date of Patent: Apr. 17, 2001

(54) METHOD OF ALIGNING THE OPTICAL AXIS OF A LASER FOR RESHAPING THE CORNEA OF A PATIENTS EYE WITH THE VISUAL AXIS OF THE PATIENT'S EYE

(76) Inventor: Herbert J. Nevyas, 2 Bala Plz., Suite PL33, Bala Cynwyd, PA (US) 19004

( * ) Notice: Subject to any disclaimer, the term of this patent is extended or adjusted under 35 U.S.C. 154(b) by 0 days.

(21) Appl. No.: 09/290,491

(22) Filed: Apr. 12, 1999

(51) Int. Cl.[7] ............................................. A61B 18/18
(52) U.S. Cl. ................................. 606/5; 606/6; 128/898
(58) Field of Search ........................... 606/4–6, 10–12, 606/17, 18

(56) References Cited

U.S. PATENT DOCUMENTS

| 4,887,592 | * | 12/1989 | Loerscher | 606/5 |
| 5,098,426 | * | 3/1992 | Sklar et al. | 606/5 |
| 5,152,759 | * | 10/1992 | Parel et al. | 606/5 |
| 5,423,801 | * | 6/1995 | Marshal et al. | 606/5 |
| 5,865,830 | * | 2/1999 | Parel et al. | 606/5 |
| 6,004,313 | * | 12/1999 | Shimmick | 606/5 |

\* cited by examiner

Primary Examiner—Michael Peffley
Assistant Examiner—Ahmed Farah
(74) Attorney, Agent, or Firm—Akin, Gump, Strauss, Hauer & Feld, L.L.P.

(57) ABSTRACT

A method of aligning the visual axis of a patient's eye with the optical axis of a beam of laser radiation for shaping the cornea by ablation includes the steps of optically folding the optical axis of a visible light laser into the optical axis of the ablation laser, aligning the optical axis of the ablation laser and the visible light laser to be both parallel and concentric where they impinge on the cornea of the patient's eye, adjusting the relative position between the patient's eye and the beam of visible radiation until the patient observes a characteristic flare around a spot of visible light.

10 Claims, 1 Drawing Sheet

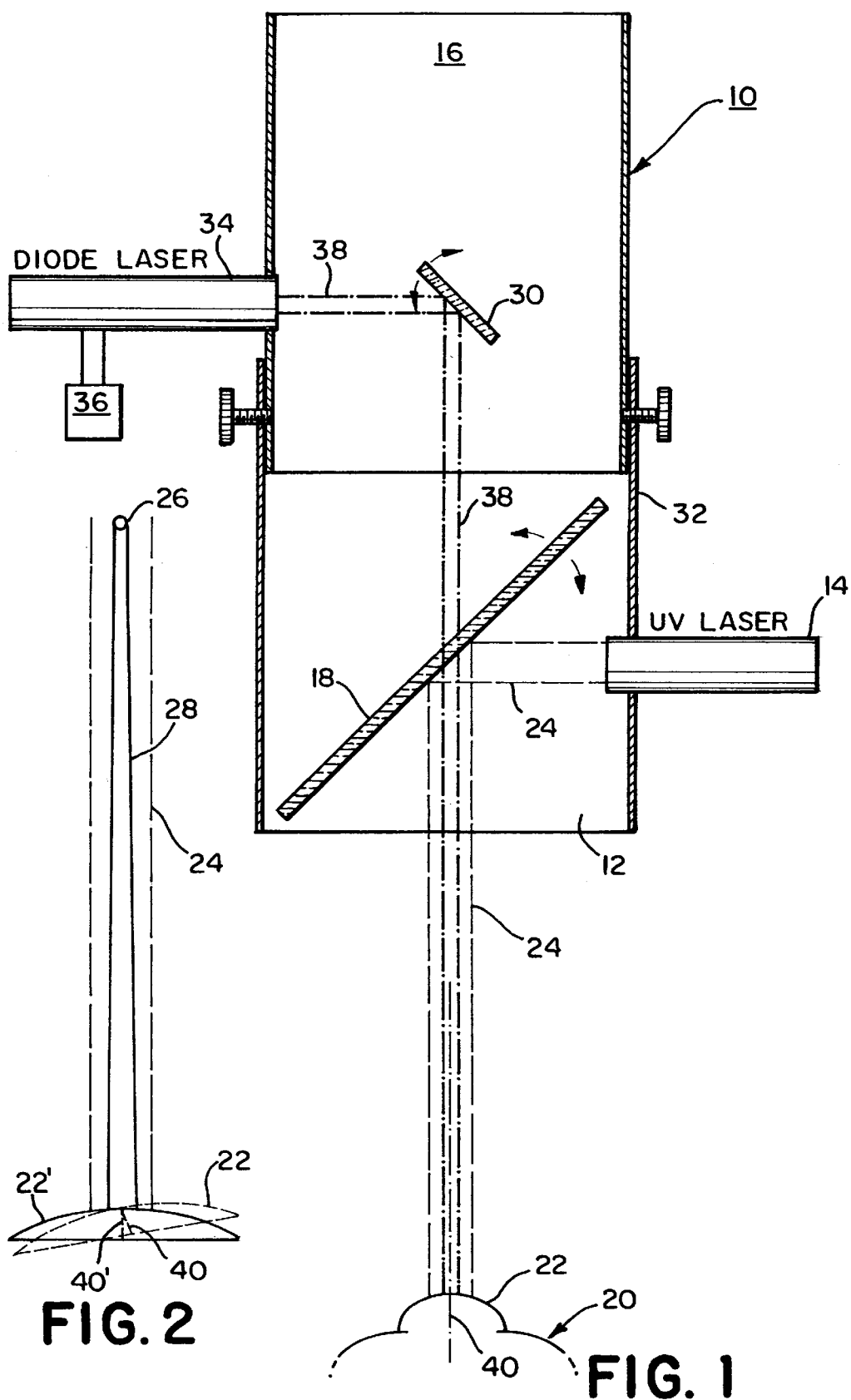

METHOD OF ALIGNING THE OPTICAL AXIS OF A LASER FOR RESHAPING THE CORNEA OF A PATIENTS EYE WITH THE VISUAL AXIS OF THE PATIENT'S EYE

FIELD OF THE INVENTION

This invention relates generally to laser keratectomy and in particular to properly aligning the visual axis of the patient's eye with the optical axis of the laser beam used to shape the cornea of the eye.

BACKGROUND OF THE INVENTION

The use of an excimer laser to reshape the cornea is now a widely practiced procedure for correcting myopia, astigmatism and hyperopia. As is known, the laser beam is shaped at a point in its pathway or scanned over the cornea to remove tissue by ablation. One of the most serious problems that can occur in any keratorefractive procedure that involves the reshaping of the central cornea is the decentration of the central region of the reshaped cornea from the point where the visual axis intersects the cornea. Such decentration is a known problem with excimer laser keratectomy including but not limited to PRK and LASIK surgery. To overcome the problem, excimer lasers conventionally provide a fixation light. The fixation light is positioned to be centered in the excimer laser beam above its last turning mirror. The optical axis of the fixation light is presumably aligned with the optical axis of the excimer laser allowing the surgeon to align the visual axis with the optical axis of the fixation light and thus presumably the optical axis of the excimer laser. However, since the fixation light can be viewed by the patient's eye when it is in a position other than directly aligned with the excimer laser beam, the ablated area may be decentered with the visual axis intersecting an area of the ablation other than at its center. This introduces astigmatism, irregular astigmatism, hyperopia, decreased visual acuity, "ghost" images and slows the postoperative recovery of vision.

Experience with excimer lasers has shown that a patient can observe the fixation light by rotation of his or her eye so that the eye's visual axis is not parallel to the laser beam. See FIG. 2. Such rotation will result in decentration of the ablation of the cornea. Accordingly, there is a need for a way to enhance centration of the cornea ablation laser with the visual axis of the eye.

Customarily, the centration of the excimer beam is accomplished by centering the pupil in the path of the excimer ablation either by marking the center of the pupil with two coincident visible laser beams which intersect at the center of the laser ablation or by positioning the pupil so that it falls inside the circle of a reticle in the eye piece of the surgeon's microscope, that reticle having previously been aligned with the excimer laser beam. The patient is then asked to look at a fixation light which has been previously calibrated to set it in the center of the excimer laser beam when the patient's eye is centered under the operating microscope. The problem with this fixation technique is that the patient's visual axis may be directed at the fixation light even when the pupil and eye are not centered in the excimer ablation beam because the eye is tilted, since the patient can still see the fixation light even when the eye is not properly centered.

Put differently, positioning the patient's eye under the laser so that the laser beam for ablating the cornea is centered symmetrically around the visual axis is essential for good optical quality of the corneal ablation. However, no matter how precisely the visual axis is lined up with a conventional fixation light, the laser's optical centration cannot be accurate unless the fixation light itself is located so that it is viewed by the patient in the center of the laser beam. Since the patient's fixation is subjective and the laser beam is invisible, assurance that the instrument has been calibrated so that the fixation light is perfectly centered with an excimer light cannot be obtained with sufficient certainty. The present invention provides assurance of proper alignment and centration between the laser beam and the patient's visual axis and allows the surgeon to align the fixation beam if necessary.

Accordingly, the present invention is directed to a method of assuring centration of the laser beam along the patient's visual axis.

DESCRIPTION OF THE PRIOR ART

U.S. Pat. No. 5,549,597 is directed to an auxiliary apparatus for enabling in situ determination of the astigmatic axis of an eye and for aligning the cylindrical axis of an excimer laser for surgery. In general, the apparatus projects an adjustable target image. The image is adjusted until it can be clearly viewed by the patient. The result is a readout of the astigmatic axis which is used to adjust the excimer laser. The light source for illuminating the projected image is a conventional electric light or a light emitting diode.

U.S. Pat. No. 4,765,336 describes an apparatus for folding a slip lamp light source into the optical axis of a laser beam. A HeNe beam is also folded into the optical axis. All three beams are said to be coaxial or can be made coaxial by use of a mechanism for moving the laser and illuminating beams as viewed through a microscope.

U.S. Pat. No. 4,583,539 is directed to a laser surgical system wherein a HeNe laser and cold light source are optically folded into the optical axis of a $CO_2$ laser. The HeNe laser is used to properly direct the $CO_2$ laser since infrared radiation emitted by the $CO_2$ laser is not visible to the human eye.

U.S. Pat. No. 5,281,211 is directed to an apparatus for aiming and/or aligning an excimer laser using a HeNe laser. In particular, a HeNe laser is used to generate visible light which is projected along the optical axis of the excimer laser. Thus the HeNe laser can be viewed through the surgical microscope by the physician.

U.S. Pat. No. 4,409,979 discloses a system for combining both observation beams and illuminating beams in a single optical system for a laser for surgically treating the eye. The light sources can be HeNe laser, a surgical laser and a non-coherent light source.

U.S. Pat. No. 4,830,483 discloses apparatus for providing a visible light guide for an excimer laser.

U.S. Pat. No. 4,881,808 is directed to a system in which a visible light source is coaxially combined with a surgical light source. U.S. Pat. No. 4,887,592 is to the same effect.

U.S. Pat. No. 5,474,548 describes a method for aligning a patient's visual line of sight with the optical axis of an ophthalmic device. The device can be one that is used during laser surgery. The mechanism and method for obtaining alignment according to this patent consists of obtaining two images and then having the patient move his or her eye until the images appear to be in alignment as viewed by the patient's eye.

U.S. Pat. No. 5,214,455 is directed to a system and method for objective eye alignment as opposed to alignment based upon a patient's report of what he or she sees. The patent describes apparatus and a method for obtaining such objective eye alignment by finding and comparing the relationship between the instrument axis and the axis of the patient's eye which is particularly defined.

U.S. Pat. No. 4,620,318 is directed to an apparatus and method using a scanning beam to describe a circular locus of points substantially centered on the fovea.

U.S. Pat. No. 5,442,412 refers to an apparatus and method for fixing the position of the eye using a ring of visible light in combination with a second light source producing a dot of visible light. The system determines when the dot and ring are not concentric.

U.S. Pat. No. 5,024,518 is directed to an ophthalmic contact lens with an external fixation light for determining when the fovea of the eye aligns with a beam of light.

SUMMARY OF THE INVENTION

The present invention relates to a method for properly positioning the patient's eye in the optical axis of a laser beam to be used for reshaping the cornea of the eye. More particularly, the present invention relates to a method of aligning the visual axis of the patient's eye with the optical axis of a laser beam for ablating the eye's cornea.

In accordance with the present invention, a low power laser producing visible light is optically coupled to the ablation laser in a manner so that the low power visible laser beam is folded into the axis of the ablation laser beam. The visible light laser beam is adjusted until it is exactly coaxial with the ablation laser beam. More particularly, the two laser beams are adjusted until the operative part of the beams, that is the part which will be incident on the eye, are both coaxial and concentric.

Next the patient is positioned so that his or her eye is on the aligned axes of the coaxial beams. Only the visible light laser is excited at this time. The relative position between the patient's eye and the aligned beams is adjusted while the patient observes the spot of light emitted by the visible light laser. If the light beam is seen merely as a spot, then the visual axis of the patient's eye is not aligned with the two aligned optical axes. When the two optical axes are aligned with the patient's visual axis, then the patient observes a characteristic flare around the spot indicating that the visible laser beam impinges directly on the patient's fovea centralis, the center of retinal fixation. This flare, which has the visual appearance of a chrysanthemum, indicates proper alignment of the eye's visual axis with the previously aligned axes. The corrective laser surgery can now proceed with knowledge that undesirable decentration will not occur.

More particularly, the present invention is directed to a method of symmetrically aligning the visual axis of a patient's eye with the optical axis of an excimer laser used to correct myopia or hyperopia by reshaping the cornea of the eye. In accordance with the present invention, a low power laser producing visible coherent light is fixed to the to the excimer laser instrument in a manner so that the visible laser beam is folded into the axis of the excimer laser beam. The visible light beam is adjusted relative to the excimer light beam until the two beams are both coaxial and concentric. Next, the patient whose eye is to be reshaped using the excimer laser is positioned with his or her eye in the optical axis of the laser apparatus. The patient gazes at the beam of light generated by the visible light laser. If the patient sees a spot, for example, a red spot, then the visual axis of the patient's eye is not aligned with the optical axis of the laser. The relative position of the eye and the apparatus are then adjusted, preferably by moving the entire apparatus, until the patient reports seeing a characteristic flare of light around the spot. The patient is directed to fixate his or her eye in this position. The large flare has been described as having the shape of a chrysanthemum. The excimer laser is activated and the cornea is then reshaped using the excimer laser.

There is significant advantages to using a visible laser light beam for alignment of the eye's visual axis with the optical axis of the laser apparatus. Among these is the fact that the spot and the special flare for indicating proper alignment is visible to the patient even when the corneal flap is lifted during LASIK surgery. When the corneal flap is lifted in LASIK surgery, patient's often have great difficulty seeing a conventional non-laser fixation light. This is not the case when using a low power visible light laser. In addition, the laser fixation beam and its special flare is visible even to patients with high refractive errors. A very high myope cannot make out a conventional light bulb, fiber optic or diode fixation light at a distance much further than his or her far-point. However, visible laser light, which takes the form of a central pencil of light in the eye's optical system, is not refracted and is seen clearly even by the very high myope.

BRIEF DESCRIPTION OF THE DRAWING

FIG. 1 is a schematic elevation view of the apparatus used to perform the present invention.

FIG. 2 is a schematic illustration of how the cornea can be decentered.

DETAILED DESCRIPTION OF THE PREFERRED EMBODIMENT

In the description which follows, like parts are indicated throughout the specification and drawings with the same reference numerals, respectively. The drawing is not necessarily to scale, and the proportion of certain parts have been exaggerated to better illustrated certain structural details.

FIG. 1 schematically illustrates the apparatus 10 for practicing the method of aligning the visual axis 40 of a patient's eye with the optical axis of a surgical laser beam 24 for ablation of the cornea. The apparatus 10 includes a conventional laser apparatus 12 for use in shaping the cornea to correct for myopia, hyperopia and other optical defects by ablation. The laser apparatus 12 includes an excimer laser 14 for generating coherent ultraviolet light used for reshaping the central cornea in accordance with known procedures such as PRK or LASIK. As is known, the laser 14 provides ultraviolet light at 193 nanometers (nm). The laser 14 is operatively coupled through the tube 32 which supports and houses a pivotable mirror 18. Mirror 18 reflects the coherent excimer radiation emitted by laser 14 downwardly onto the cornea 22 of the eye 20. Mirror 18 is pivotably mounted to adjust the portion of the excimer beam 14 for centration in the microscope reticle (not shown). The UV radiation 24 emitted by laser 14 is indicated by dash lines. It should be understood that the mirror 18 is illustrated schematically. Scanning of the excimer radiation 24 to shape cornea 22 is effected by a system of two or more turning mirrors or other optical scanning devices.

More particularly, the excimer laser beam 24 is reflected by the last turning mirror 18 which is transparent or at least partially transparent to visible light. The laser apparatus 12 may be a broad beam excimer laser. A broad beam laser has a shaping device interposed between the laser which produces the ultraviolet beam itself and the turning mirrors, such as last turning mirror 18. The beam shaper is a computer controlled shutter (not shown) that allows a certain number of pulses at a certain iris diaphragm to correct spherical myopia. The shutter also allows a certain number of pulses at particular settings of a two bladed shutter to create a cylindrical ablation. The two bladed shutter is rotatable to place the astigmatic correction at any axis in 360°. The laser apparatus 12 thus far described is conventional. Such laser apparatus may include the excimer laser manufactured by Summit Technologies or the excimer laser apparatus manufactured by Visx Inc. It should be noted, however, that the principles of the present invention are not limited to use with broad band excimer lasers as is exemplified by the Summit or Visx lasers. The principles of the present invention are equally applicable to so called excimer scanning laser systems. In such systems, a scanning mirror or the equivalent is microprocessor controlled to scan a spot and thus shape the cornea by ablation.

Although the present invention is described as being preferable adopted for use with an excimer laser, it should be understood that the invention is not so limited. Other forms of lasers, to the extent they are now available or become available for laser keratectomy, may be substituted for the excimer laser described herein for use in accordance with the claimed invention.

The excimer laser apparatus 12 is modified by incorporating a small mirror 30 pivotably mounted in the tube 16. Mirror 30 is a conventional front silvered optical mirror. Mirror 30 is pivotably mounted between the occulars of the microscope (not shown) and is operative to fold light emitted by the visible light laser 34 into the optical axis of the excimer laser beam 24. Laser 34 is a conventional diode laser such as a red diode laser manufactured by Coherent Inc. The visible light beam 38 emitted by laser 34 is, as noted, folded into and made parallel to and coaxial with the excimer laser beam 24. The two beams of coherent radiation are aligned as explained herein so as to be both concentric and parallel with each other at the point where they are incident upon the cornea of the eye 22. The power of coherent radiation beam 38 emitted by visible light laser 34 is controlled by electronic controller 36. Preferably, the visible light beam 38 is red (635 nm), although other colors can be used, is less than 1.2–0.25 micro watts, and has a diameter substantially less than the diameter of the beam 24. The power level is chosen to avoid harm to the patient's eye, and the chosen levels are well below those presently permitted by the Food and Drug Administration. Devices for controlling the power and blink rate of visible light diode lasers are known to those skilled in the art and therefore need not be described in detail. Accordingly, electronic controller 36 is illustrated schematically.

Since, in accordance with the present invention, visible light radiation beam 38 (indicated by dot-dash lines) must be observed by the patient's eye 20, mirror 18 is made transparent or semi-transparent to visible light.

Although laser 34 is preferably a red diode laser emitting light at 635 nm, it should be understood that other lasers and other colors of visible light may be used. For example, a helium/neon (HeNe) laser may be used. Moreover, other visible light colors, such as green, may be used since the invention does not depend upon the color of the coherent visible light emitting light of the laser 34.

The mirror 30 is adjustable both rectilinearly and by angulation. Accordingly, it can be adjusted so that a fine red laser beam is made both parallel to and concentric with the laser beam 24 emitted by excimer laser 14. The numeral 38 indicates the visible light laser beam emitted by laser 34 and is marked by a dot-dash line. The diameter of the red coherent radiation emitted by visible light laser 34 is substantially smaller than the diameter of the UV radiation emitted by laser 14 (e.g. about 0.25 mm to about 0.5 mm with the lower diameter being preferred).

The laser beams 24 and 38 are aligned and concentric at the point where they impinge upon the cornea 22. This is accomplished in the following manner.

The excimer beam 24 is adjusted to a constant diameter broad beam, for example, 6 mm. A single shot of the excimer laser is delivered to a photosensitive paper set at the focal point of the laser. The mirror 30 is then adjusted so that the red beam emitted by the visible laser 34 falls exactly in the center of the spot recorded on the photosensitive paper.

More particularly, the excimer beam 24 is adjusted until it lies exactly within the circular reticle in an eye piece of the surgeon's microscope at the plane of focus of the excimer laser. This is conventionally accomplished using UV sensitive paper. The visible light laser beam 38 is adjusted so it also strikes the very center of the reticle at the focal point of the excimer laser. This is accomplished by adjusting mirror 18 so the surgeon can properly position the excimer beam 24 with the reticle in the microscope eye piece. Thus, the laser beam 24 is adjusted for centration in the reticle of the surgeon's microscope in a broad beam laser system.

Next a second piece of photosensitive paper is positioned closer to the apparatus 12 and a spot from the beam 24 is recorded on the second paper. The angle of incidence and the translational position (xy) of the visible beam 38 is adjusted by mirror 30 until the beam 38 is centered in the spot recorded on the second piece of photosensitive paper. By repeating this process at two different positions along the optical axis of the beam 24 as described, the beam 38 and the excimer ultraviolet beam 24 become both parallel and concentric. The process may be repeated to confirm that the two beams are both parallel and concentric. The centration of the beam 38 with the excimer beam 24 can be checked by the surgeon before every operative procedure if desired. In this way, the surgeon knows with sufficient certainty that the laser fixation light upon which the patient is fixating with his or her fovea during the cornea shaping procedure (also know as photo-ablation) is parallel to and exactly in the center of the excimer laser beam, thereby insuring perfect centration of the ablation around the visual axis of the eye.

Thus, both the excimer beam 24 and the visible light laser beam 38 have been adjusted so that both strike the very center of the reticle in the focal plane of the excimer laser. Thus, both are parallel and concentric. The patient is now positioned so that he or she pupil is centered in the reticle, thereby being centered in the excimer beam. The patient then looks directly at the visible light fixation laser 38 which, as noted, has been previously adjusted to be parallel and concentric with the excimer laser beam. When the patient is looking directly at the laser fixation beam and sees the characteristic flare or chrysanthemum around the visible laser light, the surgeon knows that his or her fovea (the center of fixation of the retina) is looking directly at the visible laser beam, and therefore the excimer laser ablation must be centered around the anterior section of the patient's visual axis with his cornea. Thus, the excimer laser ablation is perfectly centered.

FIG. 2 illustrates how decentration can occur even though the ultraviolet excimer radiation and visible light radiation such as may be emitted by a conventional fixation lamp 26 are coaxially aligned. As shown, both radiation beams are properly incident on the cornea 22. But because the cornea 22 is tilted in respect to the optical axes of the two beams of radiation rather than aligned along the eye's visual axis 40, decentration will occur when the excimer laser beam shapes the cornea 22. In the example illustrated in FIG. 2, the patient will report being able to see a spot of light emitted by the fixation lamp 26 and the slight tilt of the cornea cannot be observed by the surgeon.

A proper aligned cornea 22' is indicated by visual axis 40' in FIG. 2.

In actual use of the apparatus described herein, the surgeon aligns the excimer laser beam with the red visible light beam emitted by the diode laser 34 in the manner described above. The patient is then prepared for surgery and his or her eye is positioned with his or her cornea 22 intersecting the optical axes of the beams 24 and 28. The visible light laser 34 is energized so that the patient sees a spot of red light. The goal is to know when the patient is looking directly at the beam of red light with his or her fovea. If the patient is not looking at the red light with his or her fovea, he or she sees just a red spot. When the patient is looking directly at the red light with his or her fovea, he or she sees a characteristic flare of red around the spot. This large flare has been described by patients as having the look of a chrysanthemum around the red spot. The presence of this large characteristic flare confirms that the patient is looking in exactly the right direction, that is, the visual axis 40 of the patient's eye is precisely aligned with the optical axis of the beam 38 which has, as noted above, been adjusted to be both parallel and concentric with the excimer laser beam.

There is a further advantage to using a visible light laser beam to achieve proper alignment of the visual axis of the patient's eye with the excimer laser beam. The beam is visible and even the characteristic flare to ascertain proper fixation is visible to the patient when the corneal flap is lifted during LASIK surgery. When using a conventional fixation light, patients often have great difficulty seeing a nonlaser fixation light such as fixation light 26. In addition, the laser fixation beam generated by the laser 34 is fully visible to patients with very high refractive errors. A very high myope cannot make out a lamp, fiber optic or conventional diode fixation light at a distance much further than his or her far-point. However, the visible radiation generated by laser 34 is not refracted and is seen clearly even by the very high myope patient.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of aligning an optical axis of a reshaping beam emitted from a laser for reshaping a cornea of an eye of a patient with a visual axis of the eye comprising the steps of:
    (a) aligning the optical axis of the reshaping beam with an optical axis of a beam of visible light emitted from a visible light laser so the reshaping beam and the beam of visible light are parallel and concentric,
    (b) positioning the eye to intersect the aligned optical axes,
    (c) directing the beam of visible light into the eye,
    (d) adjusting a relative position between the eye and the aligned optical axes to align the visual axis with the aligned optical axes, and
    (e) confirming that the visual axis of the eye is aligned with the optical axis of the reshaping beam when the patient observes a characteristic flare around a spot of light.

2. The method in accordance with claim 1 wherein the laser for reshaping the cornea is an excimer laser.

3. The method in accordance with claim 2 wherein the visible light laser is a diode laser.

4. The method in accordance with claim 1 wherein the visible light laser is a diode laser.

5. A method of aligning a visual axis of an eye of a patient with an optical axis of an ablation beam emitted from a laser for ablation of a cornea comprising the steps of:
    (a) optically directing a beam of visible light emitted from a visible light laser into an optical path of the ablation beam,
    (b) aligning the optical axis of the ablation beam and an optical axis of the beam of visible light to be parallel and concentric at least where the ablation beam and the beam of visible light are incident on the cornea,
    (c) adjusting a relative position between the eye and the aligned optical axes, and
    (d) confirming that the visual axis of the eye is aligned with the optical axis of the ablation beam when the patient observes a characteristic flare around a spot of light.

6. The method in accordance with claim 5 wherein the laser for ablation of the cornea is an excimer laser.

7. The method in accordance with claim 6 wherein the visible light laser is a diode laser.

8. The method in accordance with claim 5 wherein the visible light laser is a diode laser.

9. A method of aligning a visual axis of an eye of a patient with an optical axis of an ablation beam emitted from an excimer laser for ablation of a cornea of the eye comprising the steps of:

(a) providing an excimer laser apparatus with a visible light laser having an optical axis of a beam of visible light emitted from the visible light laser aligned with and concentric with the optical axis of the ablation beam at a point where the optical axis of the beam of visible light and the optical axis of the ablation beam are incident on the cornea, (b) directing the beam of visible light into the eye, (c) adjusting a relative position between the eye and the aligned optical axes of the ablation beam and the beam of visible light and (d) confirming that the visual axis of the eye is aligned with the optical axis of the ablation beam when the patient observes a characteristic flare around a spot of light.

10. A method of aligning a visual axis of an eye of a patient with an ablation beam emitted from an excimer laser for ablation of a cornea of the eye to correct ocular defects comprising the steps of:

(a) optically directing a beam of visible light emitted from a visible light laser into an optical path of the ablation beam, (b) aligning an optical axis of the ablation beam and the beam of visible light to be parallel and concentric at least at a point where the optical axis of the beam of visible light and the optical axis of the ablation beam are incident on the cornea, (c) adjusting a relative position between the eye and the aligned optical axes of the beam of visible light and the ablation beam, (d) confirming that the visual axis of the eye is aligned with the optical axis of the ablation beam when the patient observes a characteristic flare around a spot of light, whereby a presence of the characteristic flare indicates that the visual axis of the eye is aligned with the optical axis of the ablation beam.

* * * * *